US00PP32033P2

(12) United States Plant Patent
Allen

(10) Patent No.: US PP32,033 P2
(45) Date of Patent: Aug. 4, 2020

(54) MAPLE TREE NAMED 'RUSTYALLEN'

(50) Latin Name: *Acer buergerianum*
Varietal Denomination: RustyAllen

(71) Applicant: William Russell Allen, Winterville, GA (US)

(72) Inventor: William Russell Allen, Winterville, GA (US)

(73) Assignee: Athena Trees, Inc., Hawkinsville, GA (US)

( * ) Notice: Subject to any disclaimer, the term of this patent is extended or adjusted under 35 U.S.C. 154(b) by 0 days.

(21) Appl. No.: 16/501,901

(22) Filed: Jul. 1, 2019

(51) Int. Cl.
*A01H 5/00* (2018.01)
*A01H 6/00* (2018.01)

(52) U.S. Cl.
USPC ..... Plt./224

(58) Field of Classification Search
USPC ..... Plt./224
CPC ..... A01H 5/00; A01H 5/04; A01H 6/00
See application file for complete search history.

*Primary Examiner* — June Hwu
(74) *Attorney, Agent, or Firm* — C. A. Whealy

(57) ABSTRACT

A new and distinct cultivar of Maple tree named 'RustyAllen', characterized by its upright pyramidal tree form with upswept branch angles; vigorous growth habit; freely branching habit with numerous lateral branches providing a full and densely foliated appearance; and dark red-colored developing leaves that become dark green in color with development and bright red to dark red and occasionally orange in color during the autumn.

4 Drawing Sheets

Botanical designation: *Acer buergerianum.*
Cultivar denomination: 'RUSTYALLEN'.

BACKGROUND OF THE INVENTION

The present invention relates to a new and distinct cultivar of Maple tree, botanically known as *Acer buergerianum*, commercially referred to as Trident Maple and hereinafter referred to by the name 'RustyAllen'.

The new Maple tree is a product of a planned breeding program conducted by the Inventor in Athens, Ga. and Winterville, Ga. The objective of the breeding program is to create new Maple trees appropriate for urban landscapes that have an upright pyramidal tree form, vigorous growth habit and bright red autumn leaf color.

The new Maple tree originated from an open-pollination of an unnamed selection of *Acer buergerianum*, not patented, as the female, or seed, parent with an unknown selection of *Acer buergerianum* as the male, or pollen, parent. The open-pollination occurred in a controlled environment in Athens, Ga. in March, 2001. The new Maple tree was discovered and selected by the Inventor as a single plant from within the progeny of the stated open-pollination in a controlled environment in Winterville, Ga. in April, 2004.

Asexual reproduction of the new Maple tree by softwood cuttings in a controlled environment in Winterville, Ga. has shown that the unique features of this new Maple tree are stable and reproduced true to type in successive generations.

SUMMARY OF THE INVENTION

Trees of the new Maple have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'RustyAllen'. These characteristics in combination distinguish 'RustyAllen' as a new and distinct Maple tree:

1. Upright pyramidal tree form with upswept branch angles.
2. Vigorous growth habit.
3. Freely branching habit with numerous lateral branches providing a full and densely foliated appearance.
4. Dark red-colored developing leaves that become dark green in color with development and bright red to dark red and occasionally orange in color during the autumn.

Trees of the new Maple can be compared to trees of the female parent selection. Trees of the new Maple differ primarily from trees of the female parent selection in developing leaf color as trees of the new Maple have dark red-colored developing leaves whereas trees of the female parent selection have yellow green-colored developing leaves.

Trees of the new Maple can also be compared to trees of *Acer buergerianum* 'ABMTF', disclosed in U.S. Plant Pat. No. 16,629. Trees of the new Maple and 'ABMTF' differ primarily in the following characteristics:

1. Trees of the new Maple have smaller leaves than trees of 'ABMTF'.
2. Developing leaves of trees of the new Maple are dark red in color whereas developing leaves of trees of 'ABMTF' are yellow green in color.
3. Trees of the new Maple have darker green-colored fully developed leaves than trees of 'ABMTF'.
4. Leaves of trees of the new Maple are bright to dark red or occasionally orange in color during the autumn whereas leaves of trees of 'ABMTF' are yellow, orange red and greyed purple in color during the autumn.

5. Trees of the new Maple flower slightly earlier than trees of 'ABMTF'.

BRIEF DESCRIPTION OF THE PHOTOGRAPHS

The accompanying colored photographs illustrate the overall appearance of the new Maple tree showing the colors as true as it is reasonably possible to obtain in colored reproductions of this type. Colors in the photographs may differ slightly from the color values cited in the detailed botanical description which accurately describe the colors of the new Maple tree.

The photograph on the first sheet is a side-by-side comparison view of a typical tree of 'RustyAllen' (left) and a typical tree of 'ABMTF' (right) grown during the summer in an outdoor nursery.

The photograph on the second sheet is a side-by-side comparison close-up view of developing leaves from a typical tree of 'RustyAllen' (left) and developing leaves from a typical tree of 'ABMTF' (right).

The photograph on the third sheet is a side-by-side comparison close-up view of developing and fully developed leaves from a typical tree of 'RustyAllen' (left) and developing and fully developed leaves from a typical tree of 'ABMTF' (right).

The photograph on the fourth sheet is a side perspective view of a typical tree of 'RustyAllen' grown during the autumn in an outdoor nursery.

DETAILED BOTANICAL DESCRIPTION

The aforementioned photographs and following observations, measurements and values describe trees grown in an outdoor nursery in Hawkinsville, Ga. and under cultural practices typical of commercial Maple tree production. Trees used in the photographs and the detailed description were eight to nine years old. During the production of the trees, average day temperature was 25° C. and average night temperature was 11° C. In the following description, color references are made to The Royal Horticultural Society Colour Chart, 2007 Edition, except where general terms of ordinary dictionary significance are used.

Botanical classification: *Acer buergerianum* 'RustyAllen'.

Parentage:

*Female, or seed, parent*.—Unnamed selection of *Acer buergerianum*, not patented.

*Male, or pollen, parent*.—Unknown selection of *Acer buergerianum*, not patented.

Propagation:

*Type*.—By softwood cuttings.

*Time to initiate roots, summer*.—About four to five weeks at temperatures about 26° C. to 28° C.

*Time to produce a rooted young plant, summer*.—About ten to twelve weeks at temperatures about 26° C. to 28° C.

*Rooting habit*.—Moderately freely branching, medium density.

*Root texture*.—Fibrous.

Tree description:

*Tree form and growth habit*.—Deciduous tree with upswept branching habit and pyramidal tree form; freely branching habit with about 25 primary branches each with about ten secondary branches developing per tree; full and densely-foliated appearance; vigorous growth habit.

*Tree height*.—About 5.6 meters.

*Tree width* (*spread*).—About 3.6 meters.

*Growth rate, height*.—About 70 cm per year.

*Growth rate, caliper*.—About 1.4 cm per year.

*Bark texture*.—Woody; when developing, with small fissures and when developed with flaky plates.

*Bark color*.—When developing, close to between 197A and 198A; when developed, flaky plates, close to 198B to 198C revealing tissue that is close to 165C to 165D and 198B.

*Branch length*.—About 1.8 meters.

*Branch diameter*.—About 3.3 cm.

*Branch internode length*.—About 3.4 cm.

*Branch strength*.—Strong.

*Branch texture and luster*.—Mostly glabrous to slightly pubescent; when developing, semi-glossy becoming more matte with subsequent development.

*Lateral branch color*.—When developing, close to between 142C to 144C and when developed, close to 201A and N199A to N199B.

Leaf description:

*Arrangement*.—Opposite, simple.

*Length*.—About 6.4 cm.

*Width*.—About 5.6 cm.

*Shape*.—Palmately tri-lobed; sinuses shallow to moderately deep and divergent.

*Apex*.—Acute to acuminate.

*Base*.—Rounded to truncate.

*Margins*.—Mostly entire with shallow serrations.

*Venation pattern*.—Palmate.

*Texture and luster, upper surface*.—Smooth, glabrous; semi-glossy.

*Texture and luster, lower surface*.—Smooth, glabrous; matte.

*Color*.—When developing, upper surface: Close to 53A and 187C becoming closer to 183A with development. When developing, lower surface: Close to 184D becoming closer to 194C with development. Fully developed, upper surface: Close to between 139A and N189A; in the autumn, close to 43A, 40A, 185A and 183A and occasionally, close to 28B; venation, close to 160A. Fully developed, lower surface: Close to N138B; venation, close to 160A.

*Petioles*.—Length: About 4.2 cm. Diameter: About 1.2 mm. Texture and luster, upper and lower surfaces: Smooth, glabrous; mostly matte. Strength: Moderately strong. Color, upper surface: Close to 151A tinted with close to 173C and 179B. Color, lower surface: Close to 151A and N144A.

Flower description:

*Flower arrangement and habit*.—Simple flowers arranged in panicles with usually about 48 flowers per panicle; flowers are upright and panicles are slightly drooping.

*Fragrance*.—Faint, sweet.

*Natural flowering season*.—Plants of the new Maple begin flowering in mid to late March and flower until mid April in Georgia.

*Flower longevity*.—Individual flowers last about seven to ten days on the plant; flowers not persistent.

*Inflorescence height*.—About 4 cm.

*Inflorescence diameter*.—About 3.4 cm.

*Flower diameter*.—About 6.6 mm.

*Flower length* (*depth*).—About 4.2 mm.

*Flower buds*.—Length: About 1.5 mm. Diameter: About 1.25 mm. Shape: Roughly spherical. Texture and luster: Mostly smooth, glabrous; proximally, slightly pubescent. Color: Close to 144B.

*Petals*.—Quantity and arrangement: About four to six petals arranged in a single whorl. Length: About 2.8 mm. Width: About 1.4 mm. Shape: Obovate to oblong. Apex: Obtuse. Base: Acute. Margin: Entire; slightly to moderately undulate. Texture and luster, upper surface: Smooth, glabrous; matte. Texture and luster, lower surface: Mostly smooth, glabrous; proximally, slightly pubescent; matte. Color: When opening, upper and lower surfaces: Close to 150B. Fully opened, upper surface: Close to 150C; with development, color becoming closer to 154B. Fully opened, lower surface: Close to 150B; with development, color becoming closer to 154B.

*Sepals*.—Quantity and arrangement: About four to six sepals arranged in a single whorl. Length: About 1.4 mm. Width: About 1 mm. Shape: Oblong. Apex: Obtuse. Base: Truncate. Margin: Entire. Texture and luster, upper surface: Smooth, glabrous; matte. Texture and luster, lower surface: Mostly smooth, glabrous; proximally, slightly pubescent; matte. Color: When opening, upper and lower surfaces: Close to 149A. Fully opened, upper and lower surfaces: Close to 150A.

*Peduncles*.—Length: About 3.5 cm. Diameter: About 1.2 mm. Strength: Strong. Aspect: Mostly upright. Texture and luster: Pubescent; matte. Color: Close to between 145A to 145B.

*Pedicels*.—Length: About 5.75 mm. Diameter: About 0.5 mm. Strength: Strong. Aspect: About 45° from the peduncle axis. Texture and luster: Pubescent; matte. Color: Close to between 145A and 145B.

*Reproductive organs*.—Stamens: Quantity: About six to eight per flower. Filament length: About 0.5 mm to 0.75 mm. Filament color: Close to 145B. Anther size: About 0.5 mm by 0.75 mm. Anther shape: Ovoid. Anther color: Close to N144B. Pollen amount: Scarce. Pollen color: Close to 15B. Pistils: Quantity per flower: Two. Pistil length: About 2.5 mm. Style length: About 1.5 mm to 1.6 mm. Style color: Close to 154B. Stigma diameter: About 0.3 mm. Stigma shape: Slightly curled. Stigma color: Close to 154B. Ovary color: Close to 145A. Fruits: Length: About 2.5 cm. Diameter: About 2.5 cm to 3.25 cm. Texture: Smooth, glabrous, waxy. Color: Close to 143B to 143C; wing, close to 145C. Seeds: Quantity per fruit: About 2 to 25. Length: About 1.5 cm. Diameter: About 4.3 cm. Texture: Slightly ridged, glabrous. Color: Close to 199B and 199D.

Temperature tolerance: Trees of the new Maple have been observed to tolerate high temperatures about 43° C. and low temperatures about −14° C. and to be suitable for USDA Hardiness Zones 5 to 8.

Pathogen & pest resistance: Trees of the new Maple have been not observed to be resistant to pathogens and pests common to Maple trees.

It is claimed:

1. A new and distinct Maple tree named ‘RustyAllen’ as illustrated and described.

* * * * *

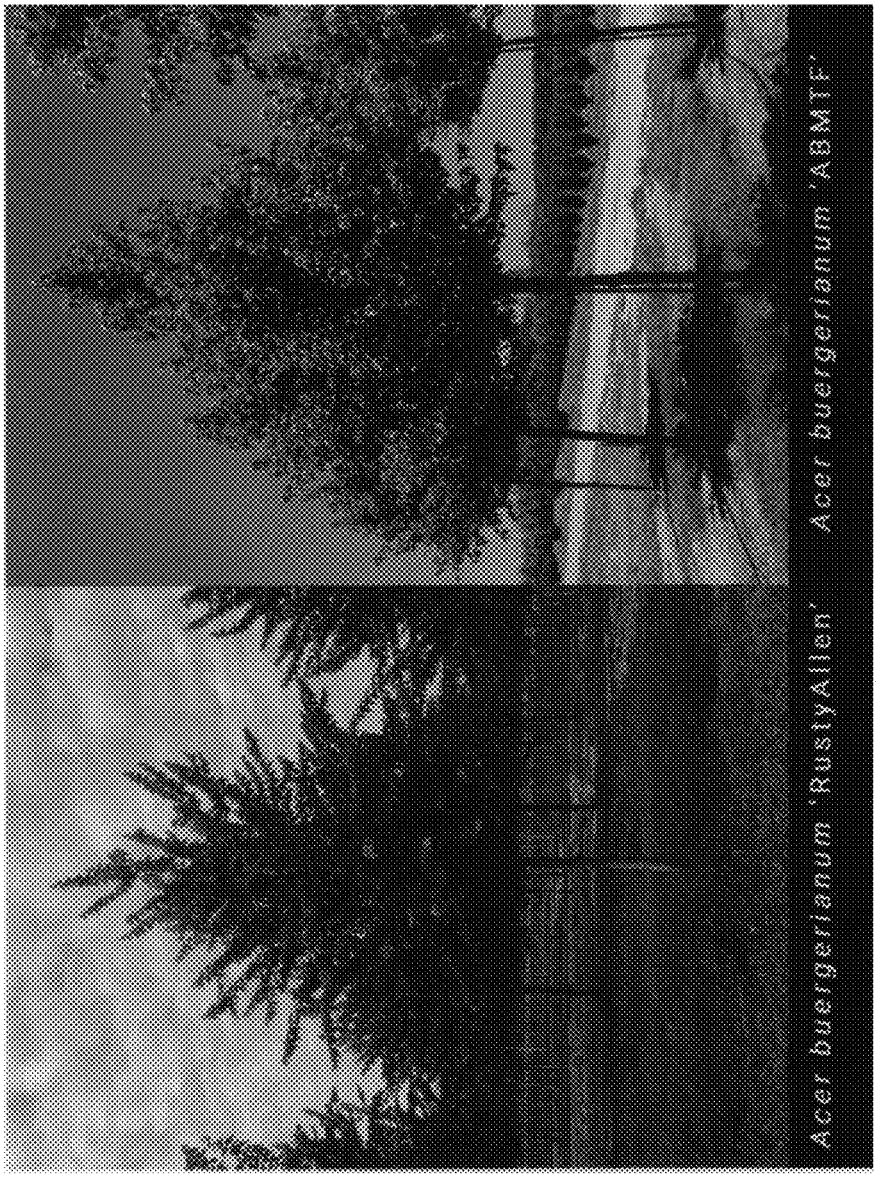
Acer buergerianum 'RustyAllen'
Acer buergerianum 'ABMTF'

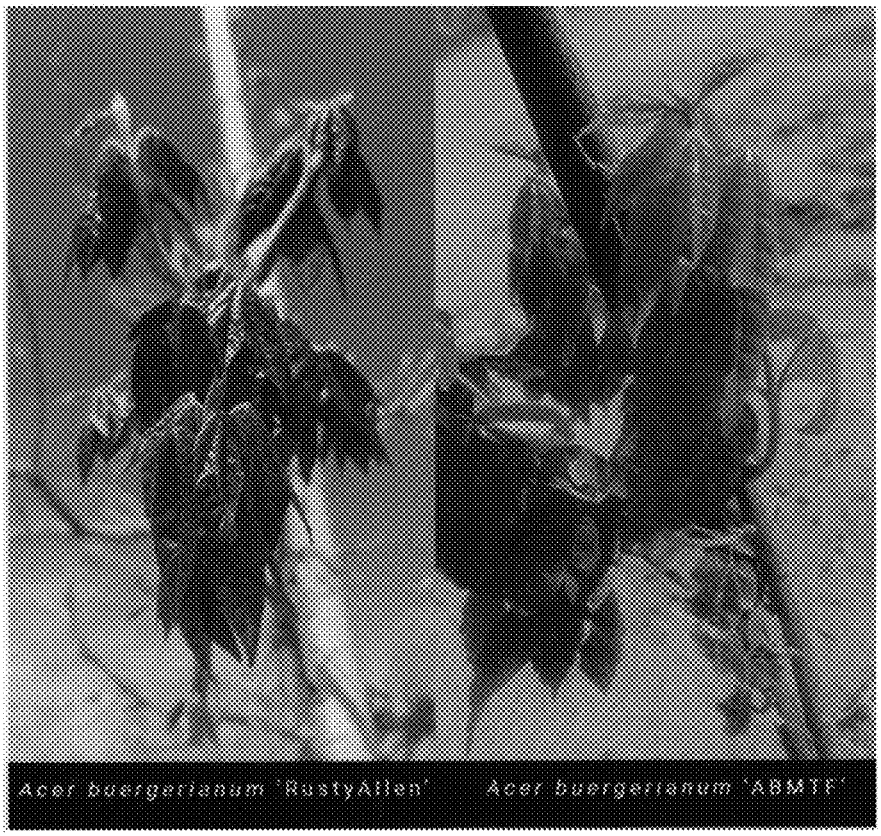
Acer buergerianum 'RustyAllen'
Acer buergerianum 'ABMTF'

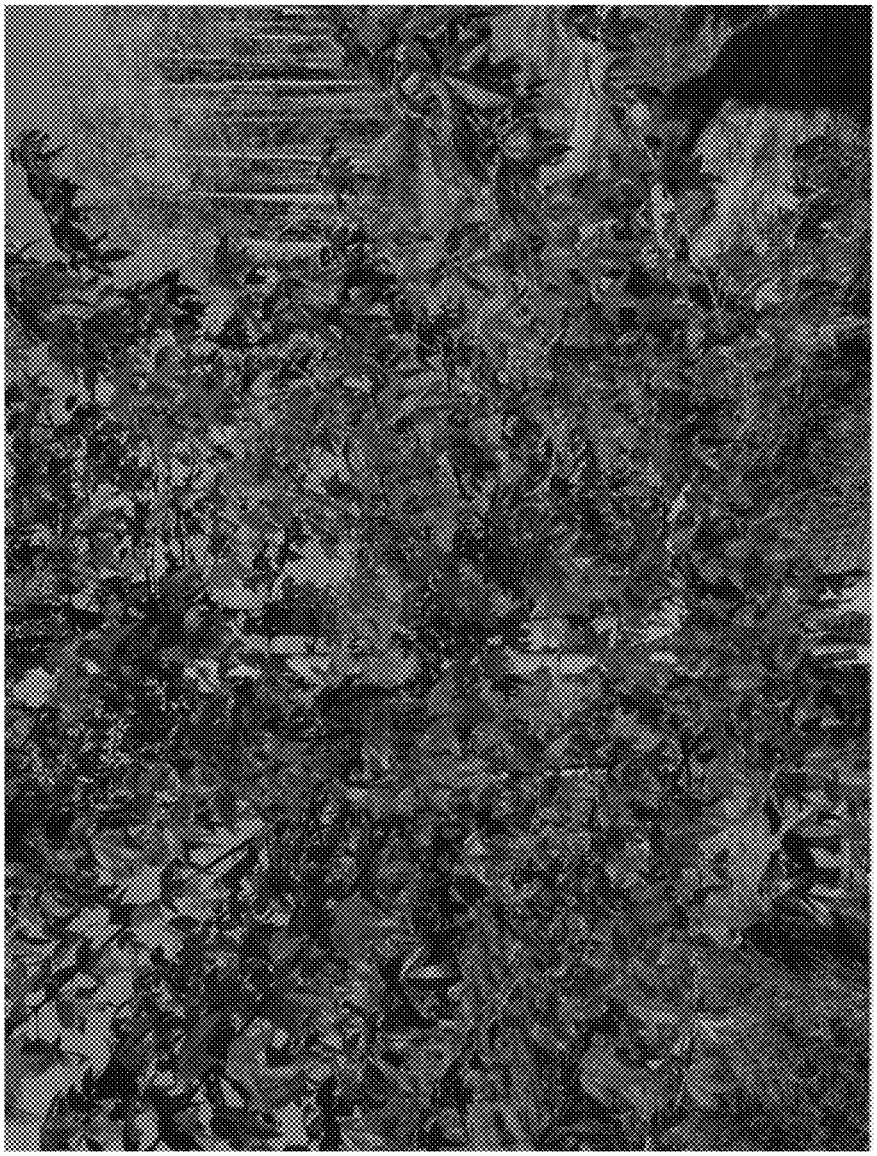

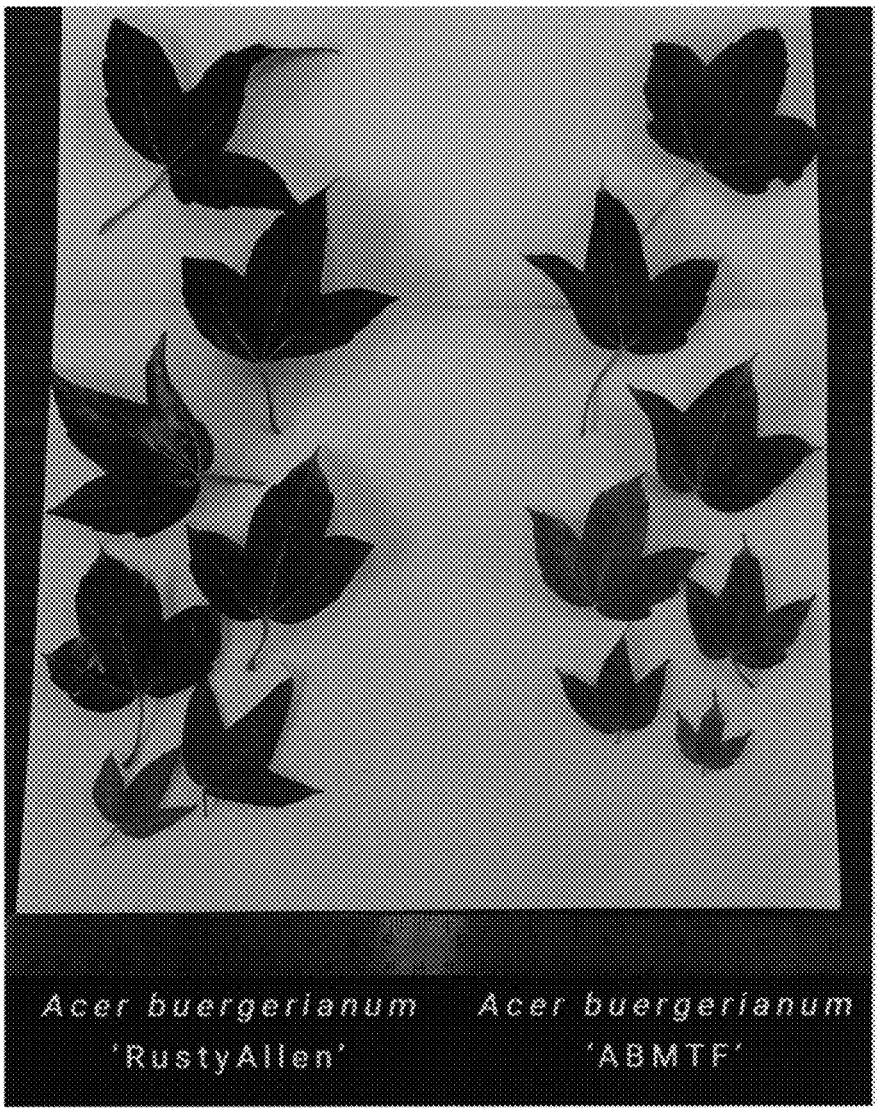
Acer buergerianum
'RustyAllen'
Acer buergerianum
'ABMTF'